(12) United States Patent
Horesh

(10) Patent No.: US 9,709,560 B2
(45) Date of Patent: Jul. 18, 2017

(54) BIOSENSORS AND BIOSENSING INCORPORATING RF AND MICROWAVE RADIATION

(75) Inventor: Moran Horesh, Nahalal (IL)

(73) Assignee: Intel Corporation, Santa Clara, CA (US)

(*) Notice: Subject to any disclaimer, the term of this patent is extended or adjusted under 35 U.S.C. 154(b) by 1982 days.

(21) Appl. No.: 12/286,383

(22) Filed: Sep. 29, 2008

(65) Prior Publication Data

US 2010/0081132 A1  Apr. 1, 2010

(51) Int. Cl.
G01N 33/543 (2006.01)
H01L 29/78 (2006.01)

(52) U.S. Cl.
CPC . *G01N 33/54373* (2013.01); *C12Q 2565/607* (2013.01); *G01N 33/5438* (2013.01); *H01L 29/78* (2013.01); *Y10S 435/817* (2013.01)

(58) Field of Classification Search
CPC ................................................ G01N 33/54373
USPC .......................................................... 422/50
See application file for complete search history.

(56) References Cited

U.S. PATENT DOCUMENTS

| 6,896,780 | B2 * | 5/2005 | Yang et al. ............... 204/408 |
| 7,560,927 | B2 * | 7/2009 | Maguire et al. .......... 324/318 |
| 2001/0027685 | A1 * | 10/2001 | Chang et al. ................ 73/590 |
| 2002/0123048 | A1 * | 9/2002 | Gau, Jr. ....................... 435/6 |
| 2003/0072549 | A1 * | 4/2003 | Facer et al. ............... 385/129 |
| 2005/0122115 | A1 * | 6/2005 | Maguire et al. .......... 324/322 |
| 2006/0020371 | A1 * | 1/2006 | Ham ................ B01L 3/502761 700/266 |
| 2007/0231790 | A1 * | 10/2007 | Su ....................... C12Q 1/6825 435/5 |

OTHER PUBLICATIONS

A. B. Copty et al., "Evidence for a Specific Microwave Radiation Effect on the Green Fluorescent Protein", Biophys. J. BioFAST, doi:10.1529/biophysj.106.084111, (2006), pp. 1-31.
I. Cosic, "Macromolecular Bioactivity: Is It Resonant Interaction Between Macromolecules?—Theory and Applications", IEEE Transactions on Biomedical Engineering, vol. 41 Issue 12 (1994), pp. 1101-1114.
A. Hassibi, "Biosensor Systems in Standard CMOS Processes: Fact or Fiction?", IEEE Transactions on Industrial Electronics, vol. 56 Issue 4 Apr. 1, 2009, pp. 979-985.

(Continued)

*Primary Examiner* — Mark Shibuya
*Assistant Examiner* — Richard Moerschell
(74) *Attorney, Agent, or Firm* — Trop, Pruner & Hu, P.C.

(57) ABSTRACT

Devices capable applying microwave and RF electromagnetic radiation to specific molecular interactions between a capture molecule and a target analyte and capable of sensing the specific molecular interaction are provided. Specific molecular interactions include, for example, specific recognition events such as, receptor-ligand, antigen-antibody, DNA-protein, sugar-lectin, RNA-ribosome, and enzyme substrate interactions and nucleic acid-nucleic acid hybridizations. Additionally, methods are provided for detecting the presence or absence of a target analyte in a sample. The presence or absence of the target analyte is detected, in part, through the detection of a binding complex between the target analyte and a capture molecule in the presence of microwave and or RF electromagnetic radiation.

22 Claims, 4 Drawing Sheets

(56) References Cited

OTHER PUBLICATIONS

H. Lee et al., "Chip-NMR biosensor for detection and molecular analysis of cells", Nature Medicine, vol. 14 Issue 8 (2008), pp. 869-874.

N. Chiu et al., "An Implantable Multifunctional Needle Type Biosensor with Integrated RF Capability", Proceedings of the 2005 IEEE Engineering in Medicine and Biology 27th Annual Conference, (2005), pp. 1933-1936.

M. Ahmadi et al., "An Efficient CMOS On-Chip Antenna Structure for System in Package Transceiver Applications", IEEE, (2007), pp. 487-490.

A. Hassibi et al., "A Programmable 0.18-um CMOS Electrochemical Sensor Microarray for Biomolecular Detection", IEEE Sensors, (2006), pp. 1380-1388.

A. Hassibi et al., "On Noise Processes and Limits of Performance in Biosensors", Journal of Applied Physics, 102 014909 (2007), pp. 014909-1-014909-12.

F. Mancinelli et al., "Non-Thermal Effects of Electromagnetic Fields at Mobile Phone Frequency on the Refolding of an Intracellular Protein: Myoglobin", Journal of Cellular Biochemistry, 93 (2004), pp. 188-196.

D. Pomerai et al., "Microwave Radiation can Alter Protein Conformation Without Bulk Heating", FEBS Letters, 543 (2003), pp. 93-97.

K. Taylor et al., "Ultra-Sensitive Detection of Protein Thermal Unfolding and Refolding Using Near-Zone Microwaves", IEEE Transactions on Microwave Theory and Techniques, vol. 53 Issue 5 (2005), pp. 1576-1586.

V. Vojisavljevic et al., "Investigation of the Mechanisms of Electromagnetic Field Interaction with Proteins", Proceeding of the 2005 IEEE Engineering in Medicine and Biology 27th Annual Conference, (2005), pp. 7541-7544.

Carolin Lau et al., "Application of heated electrodes operating in a non-isothermal mode for interference elimination with amperometric biosensors", Anal. Bioanal. Chem., (2004) 379, pp. 255-260.

\* cited by examiner

BIOSENSORS AND BIOSENSING INCORPORATING RF AND MICROWAVE RADIATION

BACKGROUND OF THE INVENTION

Field of the Invention

Embodiments of the present invention relate generally to biosensors and the detection of analyte molecules, and more specifically to devices and methods that incorporate an affinity molecule capable of specifically binding or interacting with an analyte and a module capable of providing microwave and or RF electromagnetic radiation. Embodiments of the present invention additionally relate to arrays of biomolecules and using microwave and or RF electromagnetic radiation.

Background Information

Assay methods based on molecular recognition events are ubiquitous throughout the biochemical and chemical analysis disciplines. In general, molecular recognition events are events in which a first molecule selectively forms a complex with a second molecule (or more than one molecule) through a molecular recognition event. The detection of the complex formation event can allow for the detection and quantification of an analyte from a complex mixture of species. Molecular recognition events are the foundation of biochemical interactions both in vivo and in vitro and a large variety of natural, synthetic, and semi-synthetic molecules exist that are capable of participating in a molecular recognition event. Molecules capable of participating in molecular recognition events are said to have an affinity for each other. For example, common affinity molecules include antibodies that are capable of selectively recognizing an antigen and nucleic acid hybridizations in which a first nucleic acid (such as a DNA or RNA molecule) selectively recognizes and binds to a second complementary nucleic acid.

In an exemplary antibody assay, an antibody molecule that is specific for a desired analyte is attached to a solid surface. In general antibodies are proteins that can be found in blood or other bodily fluids of vertebrates and are part of the immune system's ability to recognize and neutralize invading organisms such as bacteria and viruses. An antibody typically contains two regions that are capable of selectively recognizing an antigen molecule. The molecular recognition event has been described as a being similar to the way a lock recognizes a key. Antibodies can be produced, for example by injecting an antigen into a mammal and isolating the antibody from the blood of the mammal, or in vitro, for example, from hybridoma cells that are created from an antibody-secreting lymphocyte cell. A solution to be analyzed for the presence or absence of an analyte is contacted with the surface having an antibody attached. The solution to be analyzed is then removed from the surface of the substrate and the presence or absence of the analyte bound to the antibody on the substrate surface is detected. Commonly the presence or absence of an analyte is detected by allowing a second labeled antibody specific for the analyte of interest to react with the substrate surface, removing any un-complexed second antibody, and detecting the presence of the label (such as a fluorescent molecule). This type of assay is sometimes called a sandwich assay because the analyte is sandwiched between two antibodies. Similarly, detection of the presence of antibodies to a particular bacterium or virus in a bodily fluid from a patient can be indicative of the presence of infection by the virus or bacterium. In this case, an antigenic portion of a bacterium or virus might be immobilized on a substrate surface and the presence (or absence) of an antibody from a patient's bodily fluid that reacted with the immobilized antigen would be detected.

Molecular recognition events involving nucleic acids are commonly performed using arrays of nucleic acids that are capable of selectively recognizing complementary nucleic acids. For example, oligonucleotide microarrays can be used to monitor gene expression and discover genotypes and mutations in a massively parallel manner. Proteinaceous microarrays provide the ability, for example, to characterize the molecular progression of disease, research cellular pathways, and perform high throughput screening in drug discovery applications. Similarly, peptide-containing arrays can serve as molecular probes for a variety of biological events, such as for example, the arrays can serve as antigens for antibody-antigen systems, ligands for cell receptor-ligand systems, and substrates for enzyme-protein systems. The ability to collect large volumes of information is an integral part of biomarker discovery and the personalization of medicine. Further, other applications in bioscience, such as for example, the analysis of the proteomic content of an organism, disease detection, pathogen detection, environmental protection, food safety, and biodefense are capable of benefiting from tools that allow rapid multiplexed interrogation of analyte samples.

DETAILED DESCRIPTION OF THE INVENTION

Embodiments of the invention provide methods and devices that combine the detection of one or more molecular recognition events with the presence of RF (radio frequency) and or microwave electromagnetic wave energy. Additional embodiments provide devices and methods that combine the ability to apply RF and or microwave energy to arrays of capture molecules that are capable of participating in molecular recognition events. Additional embodiments provide arrays of capture molecules in which the array is formed on a substrate having an RF or microwave generating module located in the substrate and in close proximity to the biomolecules of the array. The application of RF or microwave energy to a molecular recognition event can effect and or enhance the selectivity of the molecular recognition event.

Generally, the sample on which an assay is to be performed to detect the presence or absence of an analyte is a complex mixture of many different species. For example, a biological specimen, such as blood, is a complex mixture of cells (which are themselves complex mixtures), proteins, peptides, minerals, ions, sugars, and hormones. Typically, even after purification procedures are performed, what is left can still be a complex mixture of different proteins, peptides, oligonucleotides, nucleic acids, and or small molecules (such as hormones, lipids, and sugars). Further, although molecular recognition events are typically highly specific processes, they can be complicated by non-specific binding events. Complications from non-specific binding events increase difficulties encountered for assays in which an analyte present in very low concentrations is to be detected. Non-specific binding events are typically referred to as "noise" in an assay. In a noisy environment, in which for example, the sample contains many biomolecules, the signal obtained from the assay may not hold enough information to allow the detection of the analyte of interest with reasonable reliability.

Embodiments of the present invention that allow the application of RF and or microwave energy (electromagnetic waves) to the locale of a molecular recognition event provide the ability to create a fine-resolution profile of a bimolecular interaction in the frequency and power domains. The application of RF and or microwave energy provides the ability to reduce the interference (or noise) created in an assay from non-specific interactions. It is known that a minor alteration in the physical, chemical, or electronic properties of a capture molecule, an analyte, or their environment changes the molecule's affinity toward its counterpart binding partner. It is therefore possible to detect the analyte by matching the strength of binding events as a function of such alteration, rather than a single event in a single set of parameter values.

Figure 1:
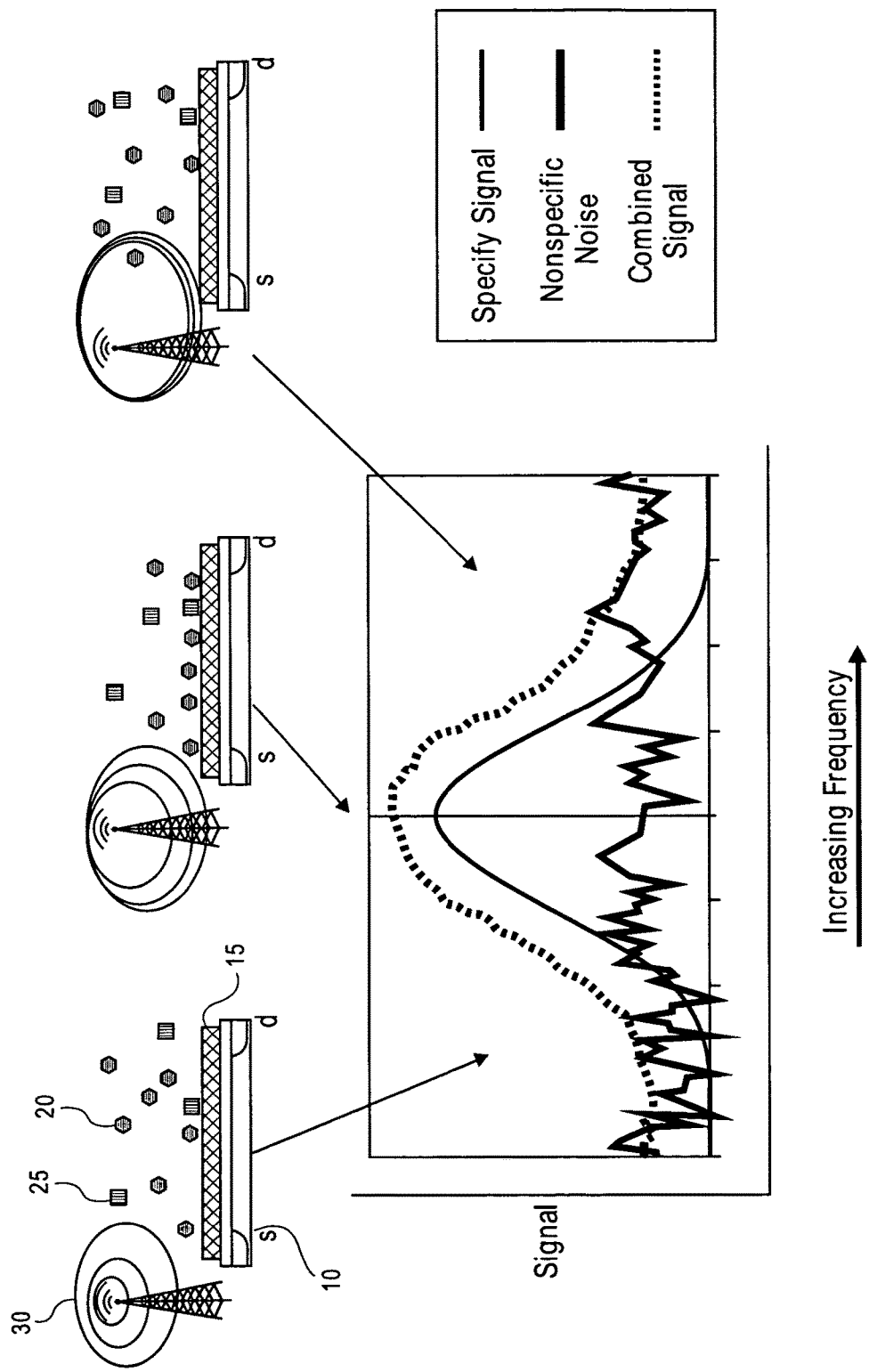
FIG. 1 diagrams a method for detecting a specific binding event occurring between a capture molecule and a target analyte on a substrate surface in which radio frequency (RF) or microwave radiation is applied to the reaction being detected.

FIG. 1 provides a diagram of an exemplary embodiment in which RF and or microwave electromagnetic waves are applied to a molecular recognition event. Aspects of this and other embodiments are described more fully herein. In FIG. 1, a substrate 10 contains capture molecules 15 on its surface. In this simplified example, the sample to be analyzed contains only two different species, 20 and 25. In an actual experiment the sample typically contains many more different components. Sample molecule 20 is a specific binding partner for the capture molecule 15. Sample molecule 25 is a molecule that is not specifically recognized by the capture molecule 15. The capture molecule 15 can be, for example, an antibody, a nucleic acid, or a receptor. If the capture molecule 15 is an antibody, then the sample molecule 20 is an antigen for the antibody. If the capture molecule 15 is a nucleic acid, then the sample molecule 20 is a complementary nucleic acid. If the capture molecule 15 is a receptor, then the sample molecule 20 is a target (or ligand) for the receptor. Other specific binding partners are possible. The sample molecules 20 and 25 are suspended in a liquid that is applied to the substrate 10 surface comprising the capture molecules 15. Microwave and or RF radiation 30 is applied in the region of the capture molecules 15 and is incident on the capture molecules 15 and any capture molecules 15 that have complexed with the recognition partner 20. Microwave or RF radiation 30 may be applied through a device that is part of the substrate or that is external to the substrate. In this example, a certain behavior of the sample molecules is diagramed as the frequency of the microwave or RF radiation 30 is varied, however other types of relative frequency-dependent behavior are possible. In this example, as the frequency of the microwave or RF radiation 30 is increased from left to right, no change in binding behavior is seen from the non-specific molecule 25. Typically, non-specific binding that is detected by an assay is considered noise. In contrast, a bell-shaped curve is observed as the frequency of the microwave or RF radiation 30 is increased from left to right, and a certain frequency is found in which the signal is maximized. Depending on the sample to be analyzed, different behaviors for the sample are observed as the frequency of the microwave or RF radiation 30 is varied. For example, the noise signal could increase or decrease as frequency is varied.

Signal detection can occur in the presence of the sample being analyzed, or the sample is removed from the substrate surface and a signal representing the state of the substrate surface, i.e., whether or not a specific binding partner has bound to the capture molecule, is collected. Optionally, signal can be collected in the absence of microwave or RF radiation 30, and then microwave or RF radiation 30 is applied locally to the substrate surface having the capture molecules and a signal is collected. The sample can be analyzed at a particular frequency or by scanning a frequency range and collecting data during the frequency scan. The signal is collected, for example, by using an electronic sensor such as a field effect transistor, an electrode capable of measuring resistance at its surface, a piezoelectric sensor, or a labeled sample in which the labeled analyte is detected on the substrate surface. Common labels that can be detected include fluorescent molecules, radioactive labels, q-dots, and nanoparticle reporters.

FIG. 1 demonstrates how changing molecular affinity with a known parameter such as the frequency of microwave or RF radiation applied to the detection assay can improve the specificity of detection for an analyte. The graph provides the sensor's response as the frequency of incident radiation is varied (in this case, increased from left to right). Other reactions that are not related to the specific recognition of the capture molecule for its target molecule are not affected or are affected in a different manner than the specific interaction. These other non-related interactions are denoted as nonspecific noise in the graph.

The effect of RF and microwave radiation on a molecular interaction is probed by varying the frequency of incident radiation and measuring the effect of the radiation on the interaction. A frequency profile for a molecular interaction similar to the one shown in FIG. 1 allows a wavelength that optimizes desired molecular interaction and signal strength (and or minimizes non-desired molecular interactions) to be selected for performing an assay for a known analyte in sample for which the behavior of the background noise as a function of radiation frequency is known. It is also possible to choose a frequency for performing an assay based on the behavior of the background noise as a function of frequency. In this case, a frequency is chosen that minimizes the interference of background noise while still providing a signal indicating the presence of the analyte. In the case of a sample for which the behavior of the analyte is known, but the behavior of the background noise is not known, scanning a range of frequencies and determining the effect on the signal received can provide information about the presence of a target analyte against the background of a noisy signal. Being of a physiological nature, the behavior of many possible molecules can be studied off-line and be kept in the database of the detection assay. Theoretically, for small concentrations of the molecules present in the sample (the common case), the number of different materials that can be detected is equal to the number of frequency points probed, as would be for a set of linear equations. See, for example, "Application of Heated Electrodes Operating in a Non-Isothermal Mode for Interference Elimination with Amperometric Biosensors", *Anal. Bioanal. Chem.*, 379:255 (2004).

The effect of microwave radiation on proteins has been described. Bimolecular interaction is strongly dependent on the activity of the individual counterparts and this can be controlled or modulated by alternating electromagnetic fields, such as microwave or RF radiation. This modulation is attributed to either conformation changes (see, for example, "Microwave Radiation can Alter Protein Conformation without Bulk Heating," *F.E.B.S. Letters*, 543:93 (2003)) and or refolding (see, for example, "Non-Thermal Effects of Electromagnetic Fields at Mobile Phone Frequency on the Refolding of an Intracellular Protein: Myoglobin," *J. Cellular Biochemistry*, 93:188 (2004)). Such results have been explained by a theoretical model (see, for example, "Investigation of the Mechanisms of Electromagnetic Field Interaction with Proteins," *Proc. 2005 IEEE, Engineering in Medicine and Biology 27th Conference*, 7541 (2005)). Additional theoretical work on the effect of electromagnetic radiation on molecular interactions is presented in "Macromolecular Bioactivity: Is It Resonant Interaction Between Macromolecules?-Theory and Applications," *IEEE Transactions on Biomedical Engineering,"* 41:1101 (1994).

Figure 2:
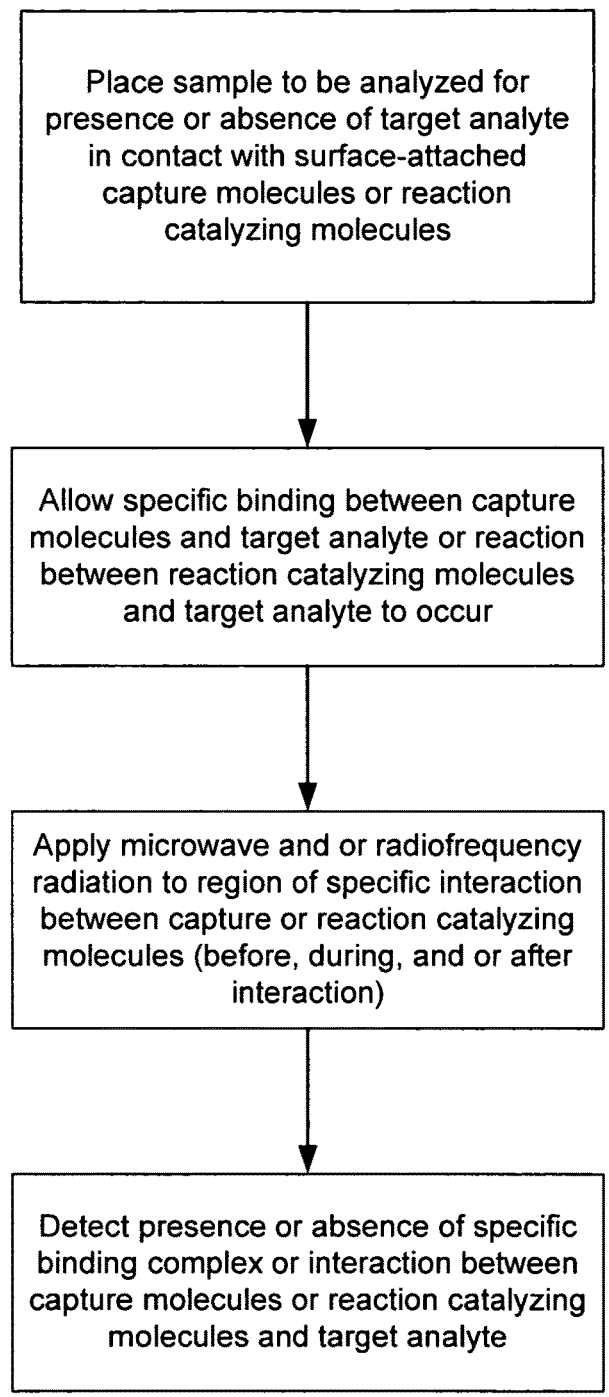
FIG. 2 diagrams a method for detecting the presence or absence of a target analyte in a sample.

FIG. 2 diagrams a method for detecting the presence or absence of a target analyte in sample. The sample to be analyzed for the presence or absence of a target analyte is placed in contact with a region of a substrate that has capture molecules capable of specifically recognizing the target analyte. In an alternate embodiment, the substrate has molecules that are capable of catalyzing a detectable reaction in the presence of the target analyte. Microwave and or RF radiation is supplied to the region of the specific interaction between the capture molecules or the reaction catalyzing molecules at one or more time points during the reaction. The presence or absence of the specific binding complex between the capture molecules or reaction catalyzing molecules and the target analyte is detected. The detection can occur before, after, and or during the application of microwave and or RF radiation. The detection can also occur at multiple points corresponding to the application of microwave and or RF radiation having different frequencies.

The integration of electronic sensors into an integrated circuit chip as described more fully herein allows for the rapid and efficient performance of assays to detect molecular interactions. The further integration of a module that is capable of generating RF and or microwave radiation fields locally to the region in which the assay is performed into the integrated circuit chip provides further efficiencies. The location of a module that is capable of generating RF and or microwaves in close proximity to the region in which the assay is to be performed on the sensor allows for the generation of a fine-resolution profile of bimolecular interaction in the frequency and power domains.

In general, microwave radiation is electromagnetic radiation having a frequency of 0.3 GHz to 300 GHz (or wavelengths ranging from 1 mm to 1 m) and RF radiation is electromagnetic radiation having a frequency of 3 Hz to 300 GHz. Frequencies that are useful for probing molecular interactions include 3 Hz to 300 GHz, 3 Hz to 1 GHz, 1 MHz to 1 GHz, 1 GHz to 100 GHz, 1 GHz to 50 GHz, 1 GHz to 15 GHz and 2.4 GHz to 2.5 GHz. In general, useful power levels for incident radiation include a specific absorption rate of less than 1.2 mW/cm$^2$ (which translates to a specific adsorption rate of less than 0.4 Watt/Kg). Power levels that are useful for probing molecular interactions additionally include 12 µW/cm$^2$ to 120 µW/cm$^2$ for sources that are in close proximity to the sample being irradiated. In general, specific adsorption rate can be converted with respect to the setup to W/cm$^2$ according to the "Radiofrequency Radiation Dosimetry Handbook," Durney et al., The University of Utah Electrical Engineering Department, 4$^{th}$ ed. (1986).

Molecular recognition or specific recognition refers to the specific interaction between two or more molecules typically through non-covalent bonding interactions such as hydrogen bonding, metal coordination, hydrophobic forces, van der Waals forces, pi-pi interactions, and or electrostatic effects. Two molecules that are able to undergo a molecular recognition event are referred to as having molecular complementarity. Molecular complementarity is sometimes thought of as being similar to the way a key fits into a lock in that a key has a specific shape that is designed for and capable of interacting with a specific lock. Examples of molecular recognition events include receptor-ligand, antigen-antibody, DNA-protein, sugar-lectin, and RNA-ribosome interactions and nucleic acid-nucleic acid hybridizations.

The terms target, target molecule, or analyte refer to a molecule of interest that is to be detected. The terms probe, probe molecule, or capture molecule refer to a molecule that selectively recognizes or binds to a target molecule or undergoes a chemical reaction with a target molecule. The probe or probe molecule generally, bur not necessarily, has a known molecular structure or sequence. Probes molecules are molecules capable of undergoing binding or molecular recognition events with target molecules.

Probes may be naturally-occurring or synthetic molecules. Probes can be employed in their unaltered state or as aggregates with other species. Examples of probes which can be employed by this invention include, but are not limited to, antibodies, peptides, proteins, enzymes, receptors, targets, pharmaceutical drugs, polynucleotides, nucleic acids, cofactors, lectins, sugars, polysaccharides, cells, cellular membranes, and organelles. The probe molecule or the target molecule can be a ligand or a receptor. A ligand is a molecule that specifically binds to another molecule, usually referred to as a receptor. Usually, the term ligand is given to the smaller of the two molecules in the ligand-receptor pair, but it is not necessary for this to be the case. A receptor can be considered to be a molecule that has an affinity for a particular ligand. Typically, in a cell, a receptor is a protein molecule to which a mobile signaling molecule can specifically bind. Cellular receptors include opiate receptors, neurotransmitter receptors, steroid receptors, intracrine peptide hormone receptors, and hormone receptors. Examples of ligands include, but are not limited to, agonists and antagonists for cell membrane receptors, toxins and venoms, viral epitopes, hormones, hormone receptors, peptides (such as neurotransmitters), cofactors, pharmaceutical drugs, lectins, sugars, polynucleotides, nucleic acids, and oligosaccharides.

The term antibody is used herein in its broadest sense to include polyclonal and monoclonal antibodies, as well as antigen binding fragments of such antibodies. An antibody useful the present invention, or an antigen binding fragment thereof, is characterized, for example, by having specific binding activity (affinity) for an epitope of an analyte. An antibody, for example, includes naturally occurring antibodies as well as non-naturally occurring antibodies, including, for example, single chain antibodies, chimeric, CDR-grafted, bifunctional, and humanized antibodies, as well as antigen-binding fragments thereof. Such non-naturally occurring antibodies can be constructed using solid phase peptide synthesis, can be produced recombinantly, or can be obtained, for example, by screening combinatorial libraries consisting of variable heavy chains and variable light chains.

In general, peptides are polymers of amino acids, amino acid mimics or derivatives, and/or unnatural amino acids. The amino acids can be any amino acids, including α, β, or ω-amino acids and modified amino acids. When the amino acids are α-amino acids, either the L-optical isomer or the D-optical isomer may be used. A peptide can alternatively be referred to as a polypeptide. Peptides contain two or more amino acid monomers, and often more than 50 amino acid monomers (building blocks).

A protein is a long polymer of amino acids linked via peptide bonds and which may be composed of one or more polypeptide chains. More specifically, the term protein refers to a molecule comprised of one or more polymers of amino acids. Proteins are essential for the structure, function, and regulation of the body's cells, tissues, and organs, and each protein has unique functions. Examples of proteins include enzymes and antibodies.

An enzyme is a protein that acts as a catalyst toward a molecule termed the enzyme substrate. An inhibitor is a substance that diminishes the rate of a chemical reaction and an activator is a substance that increases the rate of chemical reaction for a catalyzed chemical reaction. Enzyme activity can be quantitated, for example, through the application of standard kinetics analyses that typically involve the measurement of substrate and or product concentrations over time.

The term nucleotide includes deoxyribonucleotides, ribonucleotides, and analogs thereof. Analogs of nucleotides are molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can stabilize, destabilize, or enhance the specificity of hybridization with a complementary polynucleotide sequence, or enhance stability of the polynucleotide.

The terms polynucleotide, oligonucleotide, or nucleic acid refer to a polymeric form of nucleotides, either ribonucleotides or deoxyribonucleotides, that comprise purine and pyrimidine bases, or other natural, chemically or biochemically modified, non-natural, or derivatized nucleotide bases. Polynucleotides include sequences of deoxyribonucleotides (DNA) or ribonucleotides (RNA) which may be isolated from natural sources, recombinantly produced, or artificially synthesized. A further example of a polynucleotide may be peptide nucleic acid (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components.

A hybridization reaction is a process in which two single-stranded polynucleotides bind and form a stable double-stranded polynucleotide. In a hybridization event complementary nucleic acid bases pair up, and an adenine (A) pairs with a cytosine (C), and a guanine (G) pairs with a thymine (T) or uracil (U) (through, for example, standard Watson-Crick hydrogen-bonding interactions). Depending on conditions of pH, temperature, salt concentration, nucleic acids that are not absolutely complementary are able to hybridize. In general, substantially complementary nucleic acids refer to nucleic acids that have 80% or greater complementary base pairing. Highly complementary nucleic acids refer to nucleic acids having 90% or greater complementary base pairing. The proportion of the population of polynucleotides that forms stable hybrids is referred to as the degree of hybridization. Hybridization refers to the formation of double stranded species between a probe polynucleotide and a target nucleic acid wherein the probe preferentially hybridizes target nucleic acids that are substantially complementary to the probe nucleic acid and does not hybridize nucleic acids that are not substantially complementary.

The length chosen for a nucleic acid to be used as a probe molecule in an assay (such as a hybridization assay) depends on several factors, including G/C content of the sequence, positioning of mismatched bases (if any), degree of uniqueness of the sequence as compared to the population of target nucleotides, the chemical nature of the polynucleotide (e.g., methylphosphonate backbone and phosphorothioate), desired conditions for hybridization reaction (e.g., temperature and ionic strength of the solution). Typically a probe molecule will be at least 5 nucleotides and less than 75 nucleotides in length. Preferably the probe is between 24 and 60 nucleotides in length. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism.

Figure 3:
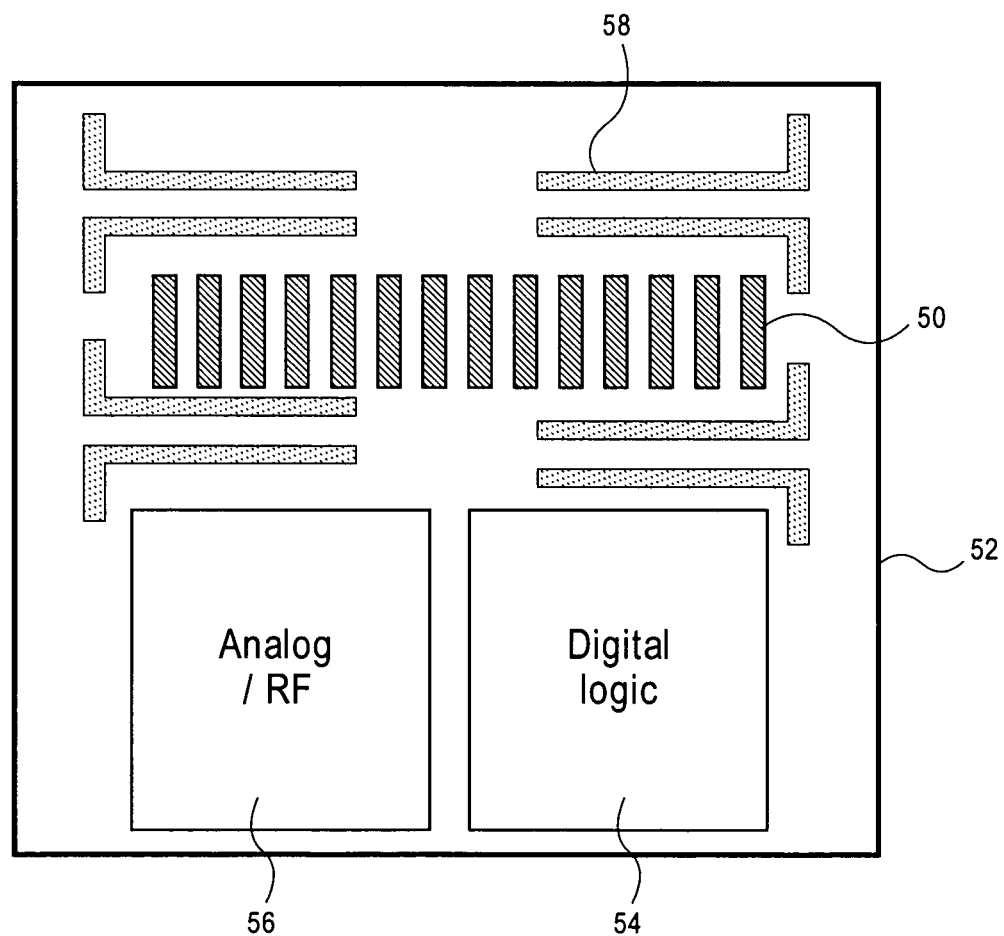
FIG. 3 provides an exemplary electronic sensor having an array of biosensing elements and an integrated module capable of generating microwave and or RF electromagnetic radiation.

FIG. 3 provides an exemplary electronic sensor having an integrated module for generating microwave and or RF electromagnetic radiation. In FIG. 3, the electronic sensor 50 is an array of electronic sensors housed on the surface of a semiconductor chip 52. The sensors 50 comprise a sensing element and an organic layer of immobilized capture molecules (not shown). The sensors are connected to electronics 56 that allow a quantitative readout indicative of the state of the capture molecules on the sensor surface of a target analyte. The state of the capture molecule on the sensor surface is, for example, complexed with a target analyte, not complexed with a target analyte, compromised in some way (through chemical reaction or other destructive process) or bound non-specifically to a molecule from the sample. The semiconductor chip 52 additionally contains electronic components 56 that are capable of providing microwave and or RF electromagnetic radiation through microwave and RF transmitting elements 58 that are localized in the vicinity of the array of sensing elements 50. Although the microwave and RF transmitting elements 58 have been shown in this exemplary embodiment as having particular shape and configuration, other shapes and configurations are possible. Transmitting elements can be located underneath and or in close proximity to where sensing is occurring. The microwave and RF transmitting elements can be constructed as metal lines operably connected to the electronic components 56 that are capable of providing microwave and or RF electromagnetic radiation. The microwave and RF generating elements typically are designed to provide microwave and RF electromagnetic radiation locally to the sensing elements.

Electronics that provide for the modulation and control of emitted RF and microwave radiation are known in the art. For example, phase-locked loops (PLLs) are very common circuits for generating very accurate RF frequencies in integrated circuits. Such circuits use an accurate reference clock at a slow rate, and control a voltage controlled oscillator (VCO) circuit, which high frequency is down converted at a known rate and matched to the reference clock. VCOs can use different techniques to generate high frequencies, such as an LC oscillator. Such circuits are described in detail in "Wireless CMOS Frequency Synthesizer Design," The Springer International Series in Engineering and Computer Science, 439 (1998). Additionally, a variety of commercially available microwave and RF generation devices exist that can be used to provide microwave and RF radiation in a localized manner to a bioassay. For example, discrete ICs such as PLL systems, power amplifiers, antennas and multiplexers are available.

A variety of detection methods are possible. For example, a binding event can be detected through the use of a label (in which the label is detected as an indication that binding has occurred) or without the use of labels. Methods of detection include, for example, using electrodes to detect changes in surface properties of the electrode such as resistance, field effect transistors, optical sensors, radiation detectors, micro- and nano-cantilevers, acoustic wave detectors, surface plasmon resonance detectors, and piezoelectric sensors. Electronic detection is the detection of a molecule through a measurement of voltage, resistance, and or current characteristics of an electronic sensor in the presence of the molecules to be detected. Typically, the electronic signal measured in the presence of the molecule to be detected is compared to an electronic signal measured in the absence of the molecules to be detected. A large variety of biosensors exist. See for example, "Biosensors and Modern Biospecific Analytical Techniques," Gorton, L., ed., Elsevier (2005). Arrays of biosensors allow highly multiplexed assays to be performed, so that a plurality of different analytes can be detected in a sample using the array.

For example, an electronic biosensor can be an electrode having a capture molecule attached to the electrode surface and electronics that allow a measurement of resistance at the electrode surface to be made. When a capture molecule that is present on the electrode surface binds an analyte, a difference in resistance at the surface of the electrode is measured. An example is "Method and Apparatus for Combined Electrochemical Synthesis and Detection of Analytes," U.S. Patent Application Publication No. 2008 0160635 A1.

Figure 4:
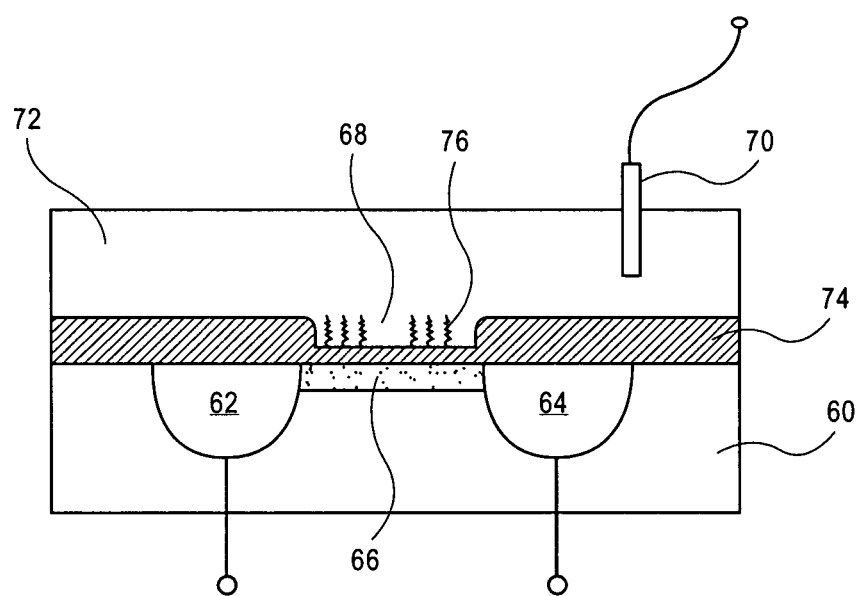
FIG. 4 provides a diagram of an exemplary electronic sensor, a field effect transistor (FET), which is capable of detecting the presence of a biomolecule and the occurrence of a molecular recognition reaction.

In an additional example, an electronic sensor can be a field effect transistor (FET) or an array of FETs. FIG. 4 shows an exemplary FET device. The FET is typically constructed on a substrate 60, such as a silicon wafer and consists of a source 62 and a drain 64 connected by an active region or channel 66. A gate region 68 controls the ability of the channel 66 to conduct electrons between the source 62 and the drain 64. For the electronic detection of biomolecules, the gate region typically is a solid-solution interface and an electrode 70 is available to the solution 72 (optionally, this electrode could be part of the chip) to apply a voltage between the electrolyte and the source 62. Electrons flow from the source 62 terminal to the drain 64 terminal if influenced by an applied voltage. In some examples, the channel region is covered by thin layer of an insulator 74, such as silicon dioxide, and the biomolecules 76 to be detected are attached to the surface of the thin insulating layer 74 facing the solution. A measurement of the drain current when a voltage is applied between the source and the drain and between the reference electrode and the electrolyte and the source provides information about the solution device interface at the location in which the biomolecule 76 is attached. Optionally, the surface of the insulating layer above the channel is functionalized for attachment and detection of the biomolecule with a polymer layer, linking molecule, and or spacing group. For example, the attachment of a single stranded DNA molecule to the surface proximate to the channel where the channel causes a change in the current through the channel that can be detected. Such devices are known in the art and are described, for example, in "Spatially Resolved Electronic Detection of Biopolymers," Physical Review E, 70:031906 (2004). The channel is typically a n-type semiconductor or a p-type semiconductor. FETs can be constructed using conventional semiconductor processing techniques. A measurement device may comprise a plurality of FETs arranged in an array and capable of performing detection in a massively parallel manner. Data is optionally gathered and analyzed using a computer. Optionally, the reference electrode is located in the substrate 60 and in contact with the solution 72.

Methods for manufacturing semiconductor chips having integrated electronics are well known in the art. Typically, for biosensors, the feature size is not a large constraint, and the feature size can be above 500 nm. For sensors, having a chip that provides low noise and low power can be more important than small feature size. The integration of microwave antennas (elements) has been described. For example, microwave and RF features are commonly integrated into chips with respect to RFID (radio frequency identification) technology. See, for example, "An Efficient CMOS On-Chip Antenna Structure for System in Package Transceiver Applications," IEEE Radio and Wireless Symposium, 487 (2007) and "Wireless CMOS Frequency Synthesizer Design," The Springer International Series in Engineering and Computer Science, 439 (1998). The microwave and or RF generating element in a chip does not need to transmit microwave energy more than 2.5 mm or even more than 1 mm in embodiments in which the transmission element is located proximally to the sensing element. Electronic sensors have been created by standard CMOS processes. See, for example, "A Programmable Electrochemical Biosensor Array in 0.18 m Standard CMOS", IEEE Sensors Journal, 6:1380 (2005). RF circuits are common in electronics and they are integrated into every processor, chipset, and telecommunication chip, even though they are sometimes not used for radio transmission, but rather to create the system clock. The RF synthesizer is integrated into the chip as it uses the native building blocks of the chip, the transistors, and sometime additional external discrete components on a printed circuit board. These may include crystal oscillators, resistors, capacitors and inductors. The output RF signal is connected to the other parts of the integrated circuits, where is may be used for applications such as system clock or a radio transmission carrier signal. Control over the RF generating circuitry is achieved through digital logic blocks as memory elements, state machines and input/output buses. They also are comprised of the same native building blocks of the chip, allowing for integration of all elements.

A wafer refers to a semiconductor substrate used in the fabrication of integrated circuits and other microdevices and is, for example, a substrate comprised of a silicon crystal. The wafer serves as a substrate for a microelectronic device having a large number of electronic features that is built through the use of nano and microfabrication techniques such as deposition of various materials, such as conductors, semiconductors, and insulators, photolithographic patterning, etching, and ion implantation. A wafer is typically diced into smaller chips.

Arrays of analyte detection sites capable of detecting a plurality of different analytes in solution can integrate the ability to apply microwave and or RF power to the array of capture regions. The arrays comprise arrays of capture molecules or probes on a substrate surface. The detection of a specific binding event can occur through a corresponding array of sensors, such as electronic sensors, or can occur through the detection of a label on the analyte or on a molecule that binds to the analyte through a second molecular recognition event (for example, a sandwich assay in which a second antibody is bound that has a label). Microwave and or RF power is applied during the detection process and signals are analyzed that contain both frequency data and signal detection data in a parallel manner for a plurality of analyte detection sites.

A variety of types of arrays of biomolecules are known, such as nucleic acid arrays and protein and peptide arrays. An array is an intentionally-created collection of molecules situated on a solid support in which the identity or source of a group of molecules is known based on its location on the array. The molecules housed on the array and within a feature of an array can be identical to or different from each other. Arrays can be made, for example, by spotting molecules of interest onto a substrate surface or by synthesizing the molecules on the substrate surface. For example, "Method and Apparatus for Combined Electrochemical Synthesis and Detection of Analytes," U.S. Patent Application Publication No. 2008-0160635 A1 and "Massively Parallel Synthesis of Proteinaceous Biomolecules," U.S. Patent Application Publication No. 2007-0122842-A1 describe methods for synthesizing biomolecules in an array on a substrate surface, although many other methods are known.

The features, regions, or sectors of an array in which molecules are located may have any convenient shape, for example, the features of the array may be circular, square, rectangular, elliptical, or wedge-shaped. In some embodiments, a feature is smaller than about 1 mm$^2$, or less than 0.5 mm$^2$. In further embodiments the features have an area less than about 10,000 µm$^2$ or less than 2.5 µm$^2$. Additionally, multiple copies of a polymer will typically be located within any feature. The number of copies of a polymer can be in the thousands to the millions within a feature. In general, an array can have any number of features, and the number of features contained in an array may be selected to address such considerations as, for example, experimental objectives, information-gathering objectives, and cost effectiveness. An array could be, for example, a 20×20 matrix having 400 regions, 64×32 matrix having 2,048 regions, or a 640×320 array having 204,800 regions. Advantageously, the present invention is not limited to a particular size or configuration for the array.

A solid support, support, or substrate is an object having a rigid or semi-rigid surface or surfaces. In some aspects at least one surface of a solid support is planar or substantially planar. The features of an array optionally form synthesis regions that are for example, wells, depressions, raised regions, pins, or etched trenches. In embodiments of the invention the substrate comprises a silicon wafer or a portion of a silicon wafer. A silicon wafer may also be referred to as a chip or a semiconductor substrate. A wafer or chip may be fashioned in various shapes and sizes. The chip could be overlaid or embedded with circuitry for driving electrodes, sensing voltages, microprocessors, memory functions, and input/output capabilities. In embodiments of the invention, the chip comprises at least surface-accessible electrodes and embedded circuitry for driving the electrodes and sensing voltages. A substrate may also be comprised of silicon, glass, nylon, plastic or other polymeric material, silicon nitride, metals, metal oxides, metal nitrides, or combinations thereof.

Capture molecules can be attached to the surface of an electronic sensor or a solid substrate according to a variety of methods. Additionally, the electronic sensing surface may be coated with thin layers of porous materials or with conducting polymers that facilitate the attachment of probes onto the surface of the sensor. For example if the sensor is a gold electrode, a probe molecule can be attached through a thiol (—SH group) linkage.

If the sensor surface is SiO$_2$ or the surface has been coated with SiO$_2$, probes may be attached to the sensor surface through the use of silane linkers (or organo silane compounds), for example. Silane linkers are molecules that have at least two different reactive groups bonded to the silane atom of the molecule: Y—R—Si—(X)$_2$. One of the reactive groups is capable of bonding to inorganic materials such as glass (SiO$_2$) and metals, the X group. These functional groups that are capable of bonding to inorganic materials are groups such as methoxy, ethoxy, chlorine, and silanolic hydroxyl groups. The second functional group is a group such as a vinyl, an epoxy, a methacryl, an amino, a mercapto, or a carboxylic acid group that is capable of forming a chemical bond to an organic material, the Y group. The R group is typically an organic group comprised of from 1 to 15 carbon atoms For example, a silanating agent, such as aminopropyltriethoxysilane (APTS) can be vapor deposited or supplied in a solution to the surface to be silanated. After reaction, the surface presents and amino group for further molecular coupling. Coupling can occur, for example, using glutaraldehyde and a molecular probe that presents an amine group for attachment. In another example, the surface could be silanated using carboxypropyltriethoxysilane and between a surface-attached carboxylic acid functional group and an amine or a thiol group of a molecular probe. In this case the coupling linker molecule can be 1-ethyl-3-(3-dimethylaminopropyl)-carbodiimide (EDC). Other coupling agents include N-Succinimidyl-3-maleimidopropionate (SMP), thiophosgene, and dithionite. See for example, Davis, H. D., Giannoulis, C. S., Johnson, R. W., Desai, T. A., *Biomaterials*, 23, 4019 (2002). Methods for coupling proteins to surface-attached functional groups are known and can be found in Aslam, M. and Dent, A., *Bioconjugation: Protein Coupling Techniques for the Biomedical Sciences*, Grove's Dictionaries, Inc., 301-316 (1998), for example. Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules. A very thin layer of oxide can be created on a metal surface, for example, by etching the metal surface with an oxygen plasma or through damascene processes.

Additional methods for signal analysis in determining whether a molecular recognition event has occurred, include, for example, labeling the sample molecules and spectroscopic methods such as UV-vis, fluorescence spectroscopy, radiation detection, surface plasmon resonance, and Raman spectroscopy. Exemplary fluorescent label molecules include, xanthene dyes, fluorescein, lissamine, phycoerythrin, rhodamine dyes, coumarin dyes, and cyanine dyes (cy3, cy5, cy7, etc.). Examples of label constructs include, radioactive labels, Q dots, metal nanoparticles, and Raman reporter particles. Raman reporter particles are metal nanoclusters having an organic molecule absorbed on or within the metal cluster or particle where the organic molecule capable of providing a unique Raman signature. The metal cluster provides a surface for enhancing the Raman signal, and the metal nanocluster provides an intrinsic surface enhanced Raman signal (SERS) from the organic molecule absorbed on or within the cluster. Microwave or RF power can be applied from a source external to the surface that the capture molecule is attached to or it can be applied through an element located in the surface that houses the assay.

In addition to probing a molecular recognition or capture event, microwave and RF radiation can be applied to improve the signal detection in other types of biosensors, such as systems that use enzymes to generate a detectable signal in the presence of an analyte. For example, a common glucose biosensor employs glucose oxidase (an enzyme) immobilized on an electrode surface and detects a product of the reaction of glucose oxidase with glucose, $H_2O_2$. The product of the reaction is detected through the oxidation of $H_2O_2$. It is also possible that an assay signal might be detected by another method, such as a different type of electronic sensor, or though the spectroscopic detection of products of the reaction, such as, for example, through UV-vis or IR spectroscopy. In the foregoing example of the detection of glucose, the product of the reaction, $H_2O_2$, can also be detected colorimetrically by employing a dye that changes color upon oxidation with $H_2O_2$. In this case of an enzyme assay, the microwave or RF power is applied locally to the region or biosensor region comprising the enzyme that catalyzed the reaction that is detected by the sensor element.

The invention claimed is:

1. A device capable of sensing a biological interaction, wherein the device comprises
   a substrate having a surface and a field effect transistor wherein the field effect transistor has a sensing surface and the sensing surface is in the substrate surface and wherein the field effect transistor is capable of sensing the occurrence of biological events at the sensing surface and wherein the biological events are an occurrence of an enzymatic catalytic reaction,
   a first module capable of generating electromagnetic radiation having a frequency in the microwave or radiofrequency range housed in the substrate, wherein the first module comprises a transmitting element connected to a circuit to cause the production of microwave or radiofrequency radiation by the transmitting element, and
   a second module for causing the first module capable of generating electromagnetic radiation to irradiate the sensing surface with a known frequency of microwave or radiofrequency electromagnetic radiation wherein the known frequency of microwave or radiofrequency electromagnetic radiation is selected to enhance a signal obtained by the field effect transistor for a molecule to be detected relative to molecules that are not to be detected; and
   an enzyme on the sensing surface capable of catalyzing a chemical reaction in the presence of a target analyte.

2. The device of claim 1 wherein the device additionally comprises capture molecules capable of specifically recognizing the analyte that are located on the sensing surface.

3. The device of claim 1 wherein the device additionally comprises capture molecules capable of specifically recognizing the analyte located on the sensing surface and the capture molecule is molecules are selected from the group consisting of nucleic acids, peptides, and antibodies.

4. The device of claim 1 wherein the first module capable of generating electromagnetic radiation having a frequency in the microwave or radiofrequency range is capable of generating radiation having a frequency from 1 GHz to 50 GHz.

5. The device of claim 1 wherein the device additionally comprises a plurality of field effect transistors that form an array.

6. The device of claim 5 wherein the plurality of field effect transistors additionally comprises capture molecules capable of specifically recognizing the analyte.

7. The device of claim 1 wherein the first module capable of generating microwave or radiofrequency radiation is capable of generating radiation that has a maximum transmission range of 2.5 mm.

8. A device capable of sensing a biological interaction, wherein the device comprises
   a substrate having a surface and a sensor wherein the sensor has a sensing element that is comprised of an electrode having a surface and the electrode is in the substrate surface and wherein the sensor is capable of sensing the occurrence of biological events at the electrode surface and wherein the electrode surface comprises capture molecules capable of specifically recognizing a target analyte,
   a first module capable of generating electromagnetic radiation having a frequency in the microwave or radiofrequency range housed in the substrate, wherein the first module comprises a transmitting element connected to a circuit to cause the production of microwave or radiofrequency radiation by the transmitting element, and
   a second module for causing the first module capable of generating electromagnetic radiation to irradiate the electrode surface with a known frequency of microwave or radiofrequency electromagnetic radiation wherein the known frequency of microwave or radiofrequency electromagnetic radiation is selected to enhance a signal obtained by the sensing element for a molecule to be detected relative to molecules that are not to be detected; and
   an enzyme on the electrode surface capable of catalyzing a chemical reaction in the presence of the target analyte.

9. The device of claim 8 wherein at least one of the capture molecules is selected from the group consisting of nucleic acids, peptides, and antibodies.

10. The device of claim 8 wherein the first module capable of generating electromagnetic radiation having a frequency in the microwave or radiofrequency range is capable of generating radiation having a frequency from 1 GHz to 50 GHz.

11. The device of claim 8 wherein the device additionally comprises a plurality of sensors that form an array of sensors.

12. The device of claim 11 wherein the plurality of sensors additionally comprises capture molecules capable of specifically recognizing the target analyte.

13. The device of claim 8 wherein the first module capable of generating microwave or radiofrequency radiation is capable of generating radiation that has a maximum transmission range of 2.5 mm.

14. A device capable of sensing a biological interaction, wherein the device comprises:
   a substrate;
   a field effect transistor (FET), which includes a sensing surface, on the substrate;
   wherein: (a)(i) the FET is capable of sensing the occurrence of biological events at the sensing surface, and (a)(ii) the biological events are an occurrence of an enzymatic catalytic reaction;
   a first module on the substrate and including at least one transmitting element;

wherein the first module and the at least one transmitting element are configured to scan electromagnetic radiation over a frequency range included within a range of 3 Hz-300 GHz;

a second module to cause the first module to scan the radiation over the frequency range and onto the sensing surface; wherein the frequency range is configured to enhance a signal obtained by the FET for a molecule to be detected relative to molecules that are not to be detected, and an enzyme on the sensing surface capable of catalyzing a chemical reaction in the presence of a target analyte.

15. The device of claim 14 comprising an array of FETs on the substrate, wherein each of the FETs has a sensing surface.

16. The device of claim 15 wherein the at least one transmitting element substantially surrounds the array in a plane.

17. The device of claim 16 wherein at least one of the at least one transmitting element is underneath the sensing surface and between the sensing surface and the substrate.

18. The device of claim 16 wherein at least one of the at least one transmitting element includes metal lines.

19. The device of claim 16 further comprising an electrode, separate from the sensing surface, which is capable of applying a voltage between an electrolyte on the sensing surface and a source of the FET.

20. The device of claim 19 comprising an insulation layer on the sensing surface.

21. The device of claim 1 wherein the first module is configured to scan electromagnetic radiation over a frequency range included within a range of 3 Hz-300 GHz.

22. The device of claim 8 wherein the first module is configured to scan electromagnetic radiation over a frequency range included within a range of 3 Hz-300 GHz.

* * * * *